(12) United States Patent
Chen

(10) Patent No.: US 10,758,866 B2
(45) Date of Patent: Sep. 1, 2020

(54) ISOLATION CHIP AND MANUFACTURING METHOD OF THE SAME

(71) Applicants: SHENZHEN WELLSIM BIOMEDICAL TECHNOLOGIES, Shenzhen (CN); WELLSIM BIOMEDICAL TECHNOLOGIES, INC, Rodeo, CA (US)

(72) Inventor: Yu-Chao Chen, Shenzhen (CN)

(73) Assignee: WELLSIM BIOMEDICAL TECHNOLOGIES, INC, Rodeo ( * ) Notice: Subject to any disclaimer, the term of this patent is extended or adjusted under 35 U.S.C. 154(b) by 0 days.

(21) Appl. No.: 16/203,649

(22) Filed: Nov. 29, 2018

(65) Prior Publication Data

US 2019/0160432 A1    May 30, 2019

Related U.S. Application Data

(60) Provisional application No. 62/593,128, filed on Nov. 30, 2017.

(30) Foreign Application Priority Data

Dec. 21, 2017   (CN) .......................... 2017 1 1396703
Oct. 31, 2018   (CN) .......................... 2018 1 1291766

(51) Int. Cl.
| | |
|---|---|
| *B01D 61/18* | (2006.01) |
| *B01D 65/08* | (2006.01) |
| *B01D 61/22* | (2006.01) |
| *B01D 69/02* | (2006.01) |
| *B01D 61/20* | (2006.01) |

(Continued)

(52) U.S. Cl.
CPC ............. *B01D 61/18* (2013.01); *B01D 61/20* (2013.01); *B01D 61/22* (2013.01); *B01D 63/088* (2013.01); *B01D 65/08* (2013.01); *B01D 69/02* (2013.01); *B01L 3/502* (2013.01); *G01N 1/4077* (2013.01); *G01N 33/57488* (2013.01); *B01D 71/025* (2013.01); *B01D 2325/021* (2013.01);

(Continued)

(58) Field of Classification Search
None
See application file for complete search history.

(56) References Cited

U.S. PATENT DOCUMENTS 5,066,283 A    11/1991   Skrabal
5,296,192 A *  3/1994   Carroll ................. G01N 33/525
                                                            422/408

(Continued)

FOREIGN PATENT DOCUMENTS

CN           105536898 A      5/2016

*Primary Examiner* — Richard C Gurtowski
(74) *Attorney, Agent, or Firm* — ScienBiziP, P.C.

(57) ABSTRACT

A device, system, and method for separating, concentrating, and isolating target particles from a bioliquid sample includes a sample reservoir, a first filtration membrane, a second filtration membrane, a first chamber, and a second chamber. The first chamber with first outlet is connected to the sample reservoir through the first filtration membrane. The second chamber with second outlet is connected to the sample reservoir through the second filtration membrane. Negative pressures are applied alternately to the two filtration membranes to isolate target particles, clogging of the membranes being prevented by the same alternating but opposite-phase positive pressures.

13 Claims, 17 Drawing Sheets

(51) Int. Cl.
*G01N 33/574* (2006.01)
*B01L 3/00* (2006.01)
*B01D 63/08* (2006.01)
*G01N 1/40* (2006.01)
B01D 71/02 (2006.01)
G01N 3/00 (2006.01)

(52) U.S. Cl.
CPC ........ *B01L 2300/0681* (2013.01); *G01N 3/00* (2013.01); *G01N 2001/4088* (2013.01)

(56) References Cited

U.S. PATENT DOCUMENTS

| | | |
|---|---|---|
| 2003/0134416 A1 | 7/2003 | Yamanishi et al. |
| 2006/0212021 A1* | 9/2006 | Yazaki ............. A61B 5/150022 604/500 |
| 2016/0219870 A1* | 8/2016 | Wang ................. A61B 5/15003 |
| 2017/0067803 A1* | 3/2017 | Jackson ........... A61B 5/150755 |

* cited by examiner

ISOLATION CHIP AND MANUFACTURING METHOD OF THE SAME

FIELD

The subject matter herein generally relates to biotechnology, and more particularly, to an isolation chip and a manufacturing method of the isolation chip.

BACKGROUND

A biopsy of human liquid, such as urine, saliva, pleural effusion, and cerebrospinal liquid, is the sampling and analysis of the bioliquid. With isolation and study of specific biomarkers in the bioliquid, liquid biopsy can be used as a diagnostic and monitoring tool for diseases such as cancer, with the added benefit of being largely non-invasive. The specific biomarkers in the bioliquid include circulating tumor DNA (ctDNA), circulating tumor cells (CTCs), and microvesicles (i.e. exosomes). The study of CTCs and exosomes is helpful to obtain information from different perspectives, and thus improve the precision of liquid biopsy.

The existing approaches to isolation and purification of CTCs and exosomes include centrifuging, testing immuno-affinities, and filtering. However, centrifuging may cause mechanical damages to CTCs and exosomes, and is limited in throughput for clinical applications. Immuno-affinity relies on antibodies which results in higher cost, and the release process after immune-affinity may reduce the viability of CTCs and exosomes. Filtering is low cost and has high throughput, and the biological sample after filtration has good viability. However, clogging of the filtration membrane usually happens during filtration, which can decrease the isolation efficiency and purity of CTCs and exosomes.

Therefore, there is room for improvement in the art.

BRIEF DESCRIPTION OF THE DRAWINGS

Implementations of the present disclosure will now be described, by way of embodiments only, with reference to the attached figures.

DETAILED DESCRIPTION

Figure 1:
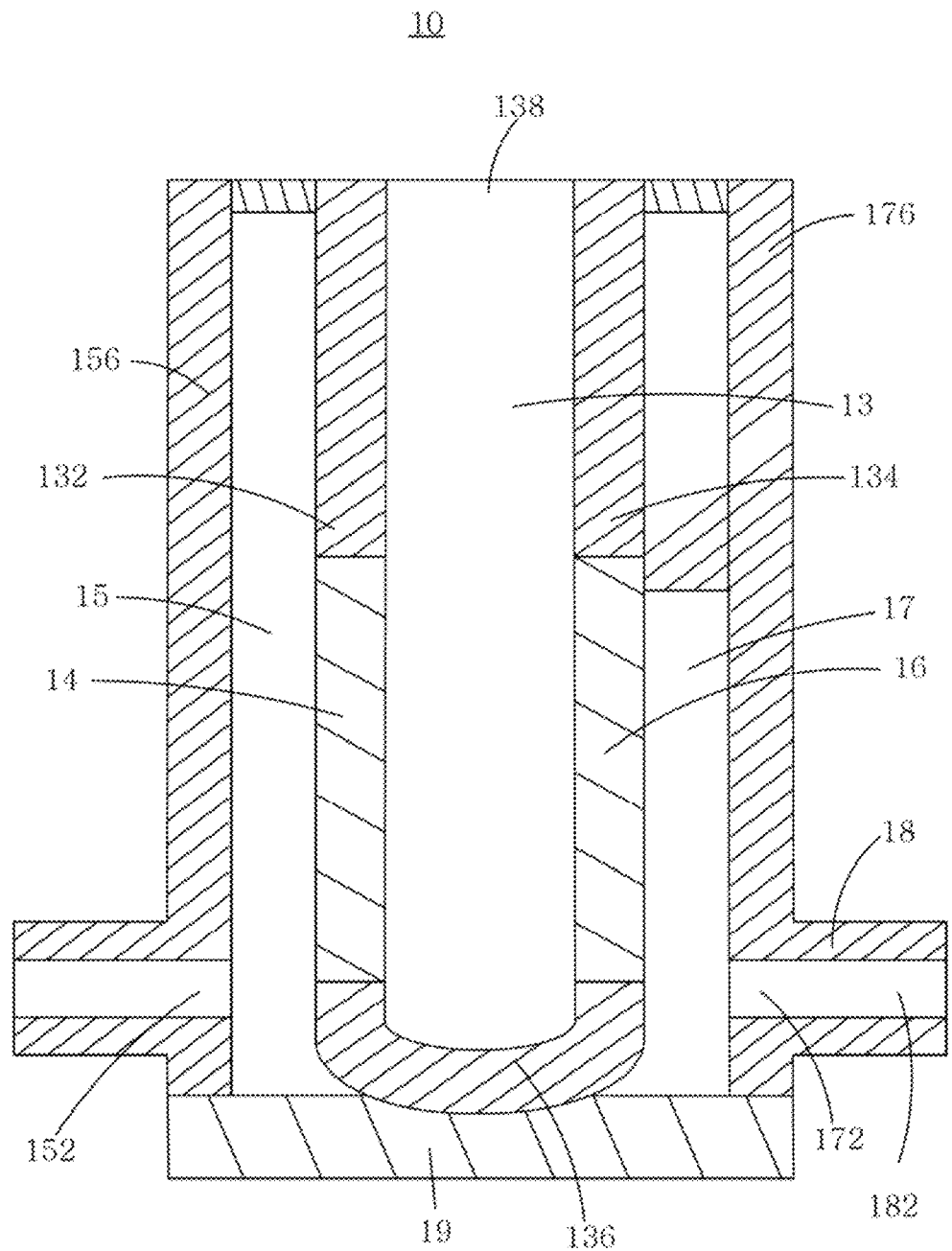
FIG. 1 is a diagrammatic view of an embodiment of an isolation chip according to the present disclosure.

It will be appreciated that for simplicity and clarity of illustration, where appropriate, reference numerals have been repeated among the different figures to indicate corresponding or analogous components. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising," when utilized, means "including, but not necessarily limited to"; it specifically indicates open-ended inclusion or membership in the so-described combination, group, series, and the like.

Figure 2:
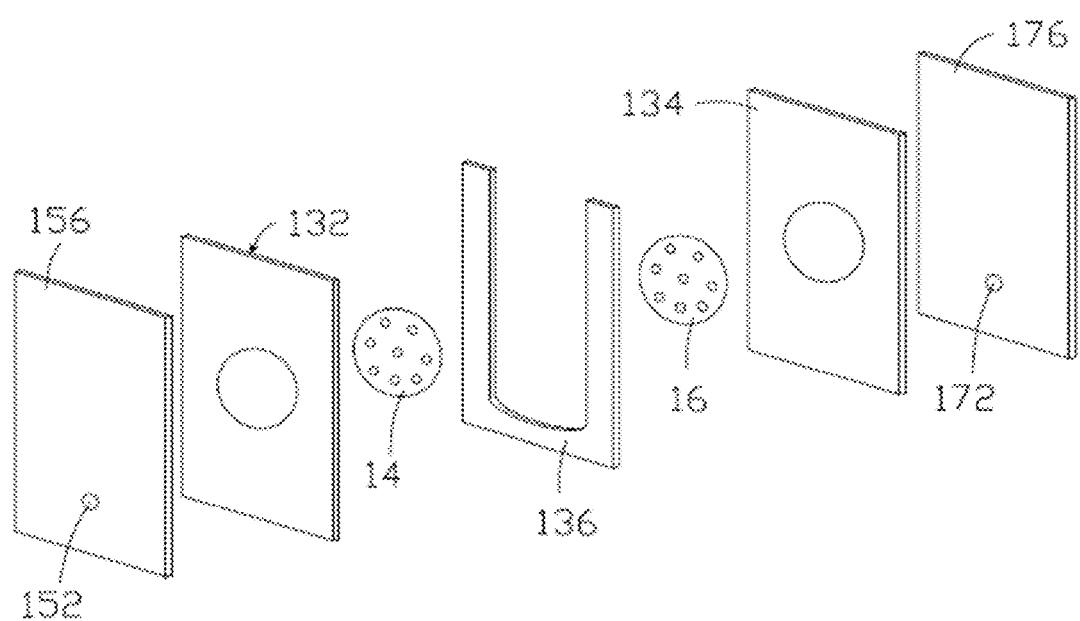
FIG. 2 is an exploded view of the isolation chip of FIG. 1.

FIGS. 1 and 2 illustrate an embodiment of an isolation chip 10 adapted for isolation and purification of target particles from a liquid sample. The liquid sample can be a bioliquid such as plasma, serum, saliva, urine, and lavage. The target particles can be biological cells such as circulating tumor cells (CTCs) or exosomes. The target particles can also be other particles such as synthesized liposomes or nanospheres.

The isolation chip 10 includes a sample reservoir 13, a first chamber 15, a second chamber 17, a first filtration membrane 14, and a second filtration membrane 16. The first chamber 15 and the second chamber 17 are positioned at opposite sides of the sample reservoir 13. The first chamber 15 is connected to the sample reservoir 13 by the first filtration membrane 14. The first chamber 15 includes a first outlet 152 that connects the first chamber 15 to an ambient environment. The second chamber 17 is connected to the sample reservoir 13 by the second filtration membrane 16. The second chamber 17 includes a second outlet 172 that connects the second chamber 17 to the ambient environment.

In an embodiment, the sample reservoir 13 includes a reservoir substrate 136, a first inner cover 132, and a second inner cover 134. The reservoir substrate 136 is substantially U-shaped, and has a certain thickness. The first inner cover 132 and the second inner cover 134 are positioned at opposite sides of the reservoir substrate 136. The reservoir substrate 136, the first inner cover 132, and the second inner cover 134 cooperatively define a receiving space (not labeled) to receive the liquid sample. The first filtration membrane 14 is attached to the first inner cover 132. The second filtration membrane 16 is attached to the second inner cover 134. Referring to FIG. 2, in an embodiment, each of the first inner cover 132 and the second inner cover 134 define a through hole (not labeled). The first filtration membrane 14 and the second filtration membrane 16 are fixedly received in the through holes of the first inner cover 132 and the second inner cover 134, respectively. Furthermore, the sample reservoir 13 defines an inlet 138 on the top. The liquid sample can be added to or removed from the sample reservoir 13 through the inlet 138.

In use, the liquid sample is added to the sample reservoir 13. Each of the first outlet 152 and the second outlet 172 is connected to a vacuum unit 30 (shown in FIG. 6). When the vacuum unit 30 generates a negative pressure in the first chamber 15 through the first outlet 152, compositions in the liquid sample that are smaller than the pores of the first filtration membrane 14 can enter the first chamber 15 through the first filtration membrane 14. When the vacuum unit 30 generates a negative pressure in the second chamber 17 through the second outlet 172, compositions in the liquid sample that are smaller than the pores of the second filtration membrane 16 can enter the second chamber 17 through the second filtration membrane 16. Since a negative pressure is alternately applied in the first chamber 15 and the second chamber 17, the compositions in the liquid sample can alternately flow through the first filtration membrane 14 and the second filtration membrane 16. This leaves the target particles that are larger than the pores of the first filtration membrane 14 and the second filtration membrane 16 in the sample reservoir 13. Furthermore, some of the target particles that are absorbed on the first filtration membrane 14 and the second filtration membrane 16 can be flushed out under the negative pressure, thereby avoiding clogging of the first filtration membrane 14 and the second filtration membrane 16.

The first filtration membrane 14 and the second filtration membrane 16 can be made of ceramic, plastic, or metal. In an embodiment, the first filtration membrane 14 and the second filtration membrane 16 can be made of anodic aluminum oxide (AAO), polycarbonate, acetate fibers, polyethylene, polypropylene, polystyrene, and any combination thereof. The first filtration membrane 14 and the second filtration membrane 16 can be made of a same material or different materials. Furthermore, the first filtration membrane 14 and the second filtration membrane 16 can have a same average pore size or different pore sizes. In an embodiment, both the first filtration membrane 14 and the second filtration membrane 16 are made of anodic aluminum oxide that have a high porosity and an average pore size.

The pore sizes of the first filtration membrane 14 and the second filtration membrane 16 can be varied according to the type of the liquid sample and the type of the target particles. In an embodiment, the pore sizes of the first filtration membrane 14 and the second filtration membrane 16 are between 2 μm and 20 μm. Preferably, the pore sizes of the first filtration membrane 14 and the second filtration membrane 16 are between 5 μm and 10 μm. More preferably, the pore sizes of the first filtration membrane 14 and the second filtration membrane 16 are 8 μm, thus the first filtration membrane 14 and the second filtration membrane 16 can isolate CTCs from a plasma sample. In another embodiment, the pore sizes of the first filtration membrane 14 and the second filtration membrane 16 are between 5 μm and 200 μm. Preferably, the pore sizes of the first filtration membrane 14 and the second filtration membrane 16 are between 10 μm and 100 μm. More preferably, the pore sizes of the first filtration membrane 14 and the second filtration membrane 16 are 20 μm, thus the first filtration membrane 14 and the second filtration membrane 16 can isolate exosomes from a plasma sample.

When the surfaces of the first filtration membrane 14 and the second filtration membrane 16 are not modified, the isolation chip 10 may also isolate non-exosomal proteins that have similar sizes and densities as those of the exosomes from the liquid sample. The non-exosomal proteins include high density lipoproteins (HDLs), low density lipoproteins (LDLs), intermediate density lipoproteins (IDLs), very low density lipoproteins (VLDL), and chylomicrons. In an embodiment, the surfaces of the first filtration membrane 14 and the second filtration membrane 16 can be chemically modified by specific biological macromolecules, such as antibodies, antigens, peptides, or chip base sequences, to allow the isolation chip 10 to isolate specified target particles.

In an embodiment, the first chamber 15 includes a first side cover 156 facing away from the first inner cover 132. The first side cover 156 and the first inner cover 132 cooperatively define the first chamber 15. The first outlet 152 is defined in the first side cover 156. The second chamber 17 includes a second side cover 176 facing away from the second inner cover 134. The second side cover 176 and the second inner cover 134 cooperatively define the second chamber 17. The second outlet 172 is defined in the second side cover 176. Furthermore, each of the first side cover 156 and the second side cover 176 can include an outlet connecting block 18. The outlet connecting block 18 defines a channel 182 aligned with the first outlet 152 or the second outlet 172. The isolation chip 10 can further include a chip base 19. The chip base 19 closes ends of the first chamber 15 and the second chamber 17 opposite to the inlet 138. The isolation chip 10 can have a symmetric or an asymmetric structure.

The reservoir substrate 136, the first inner cover 132, the second inner cover 134, the first side cover 156, and the second side cover 176 can be made of plastic, glass, metal, or composite materials. In an embodiment, the reservoir substrate 136, the first inner cover 132, the second inner cover 134, the first side cover 156, and the second side cover 176 are made of polyethyleneimine (PEI) or poly(methyl methacrylate) (PMMA).

Figure 3:
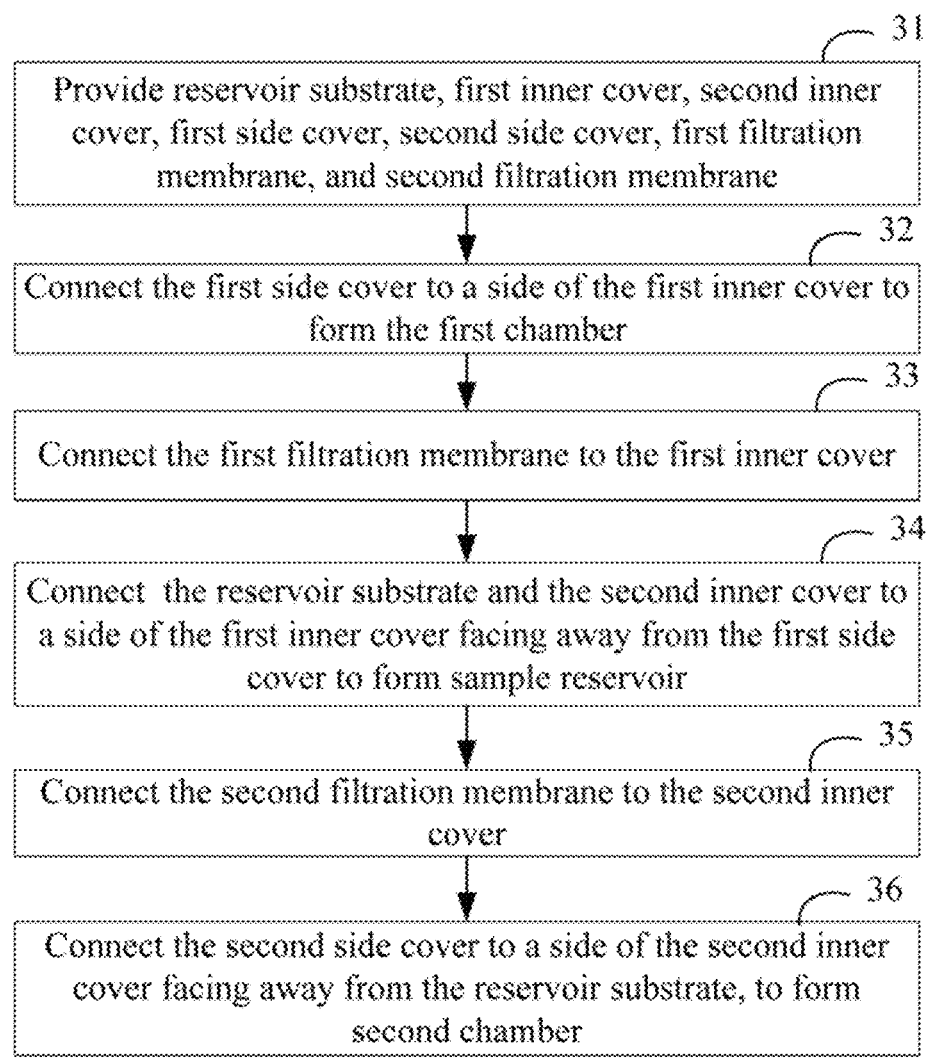
FIG. 3 is a flowchart of an embodiment of a manufacturing method of the isolation chip of FIG. 1.

FIG. 3 illustrates an embodiment of a manufacturing method of the isolation chip 10. The method is provided by way of embodiments, as there are a variety of ways to carry out the method. The example method can begin at block 31.

At block 31, the reservoir substrate 136, the first inner cover 132, the second inner cover 134, the first side cover 156, the second side cover 176, the first filtration membrane 14, and the second filtration membrane 16 are provided.

At block 32, the first side cover 156 is connected to a side of the first inner cover 132 to form the first chamber 15.

At block 33, the first filtration membrane 14 is connected to the first inner cover 132.

At block 34, the reservoir substrate 136 and the second inner cover 134 are successively connected to a side of the first inner cover 132 facing away from the first side cover 156, to form the sample reservoir 13.

At block 35, the second filtration membrane 16 is connected to the second inner cover 134.

At block 36, the second side cover 176 is connected to a side of the second inner cover 134 facing away from the reservoir substrate 136, to form the second chamber 17. The isolation chip 10 is obtained at a low manufacturing cost.

In an embodiment, the reservoir substrate 136, the first inner cover 132, the second inner cover 134, the first side cover 156, the second side cover 176, the first filtration membrane 14, and the second filtration membrane 16 are connected to each other by adhesive. The adhesive can be ultraviolet-cured adhesive or silicone adhesive.

Figure 4:
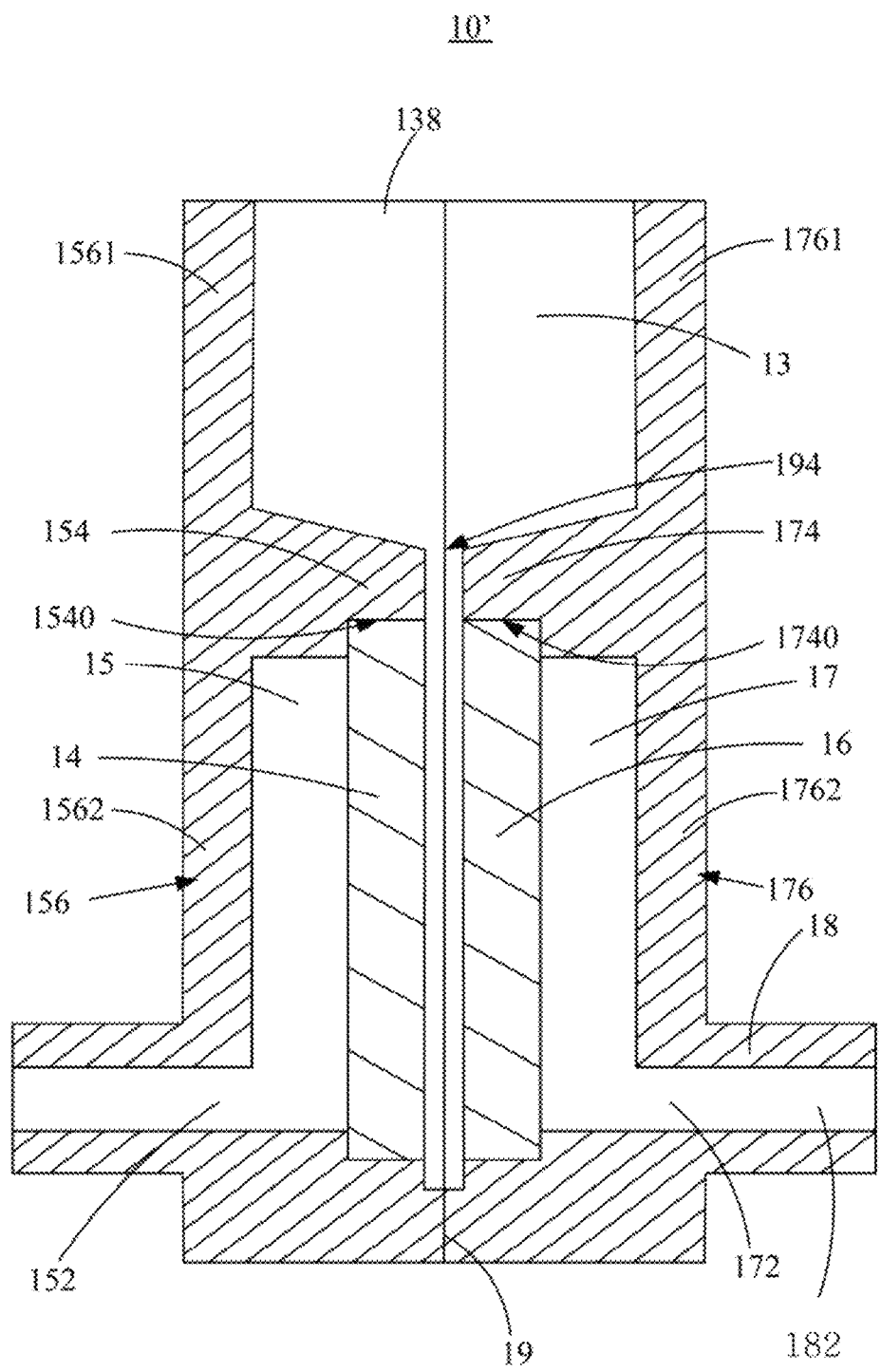
FIG. 4 is a diagrammatic view of another embodiment of an isolation chip.

FIG. 4 illustrates another embodiment of an isolation chip 10'. In the isolation chip 10', the reservoir substrate 136, the first inner cover 132, and the second inner cover 134 are omitted. Thus, the manufacturing cost can further be decreased. In this embodiment, the first side cover 156 includes a first protruding block 154. The first protruding block 154 divides the first side cover 156 into a first cover portion 1561 and a second cover portion 1562 which are at opposite sides of the first protruding block 154. The second side cover 176 includes a second protruding block 174 facing the first protruding block 154. The second protruding block 174 divides the second side cover 176 into a third cover portion 1761 and a fourth cover portion 1762 which are positioned at opposite sides of the second protruding block 174. The first cover portion 1561, the third cover portion 1761, the first protruding block 154, and the second protruding portion 174 cooperatively define the sample reservoir 13.

The isolation chip 10' further differs from the isolation chip 10 in that the isolation chip 10' includes two chip bases, that is, a first chip base and a second chip base (both labeled 19 in FIG. 3). The first chip base 19 is connected to an end of the first side cover 156, and faces the first protruding block 154. The first filtration membrane 14 is connected between the first protruding block 154 and the first chip base 19, and faces the second cover portion 1562. The second cover portion 1562, the first filtration membrane 14, and the first chip base 19 cooperatively define the first chamber 15. The second chip base 19 is connected to an end of the second side cover 176, and faces the second protruding block 174. The second filtration membrane 16 is connected between the second protruding block 174 and the second chip base 19, and faces the fourth cover portion 1762. The fourth cover portion 1762, the second filtration membrane 16, and the second chip base 19 cooperatively define the second chamber 17. In an embodiment, a gap 194 is defined between the first protruding block 154 and the second protruding block 174. The liquid sample can flow out of the sample reservoir 13 through the gap 194, and further flow into the first chamber 15 or the second chamber 17 through the first filtration membrane 14 or the second filtration membrane 16. In an embodiment, a surface of the first protruding block 154 facing the first chip base 19 defines a first mounting groove 1540. A surface of the first chip base 19 facing the first protruding block 154 defines a second mounting groove (not labeled). Opposite sides of the first filtration membrane 14 are fixedly received in the first mounting groove 1540 and the second mounting groove respectively. Similarly, a surface of the second protruding block 174 facing the second chip base 19 defines a third mounting groove 1740. A surface of the second chip base 19 facing the second protruding block 174 defines a fourth mounting groove (not labeled). Opposite sides of the second filtration membrane 16 are fixedly received in the third mounting groove 1740 and the fourth mounting groove respectively.

Figure 5:
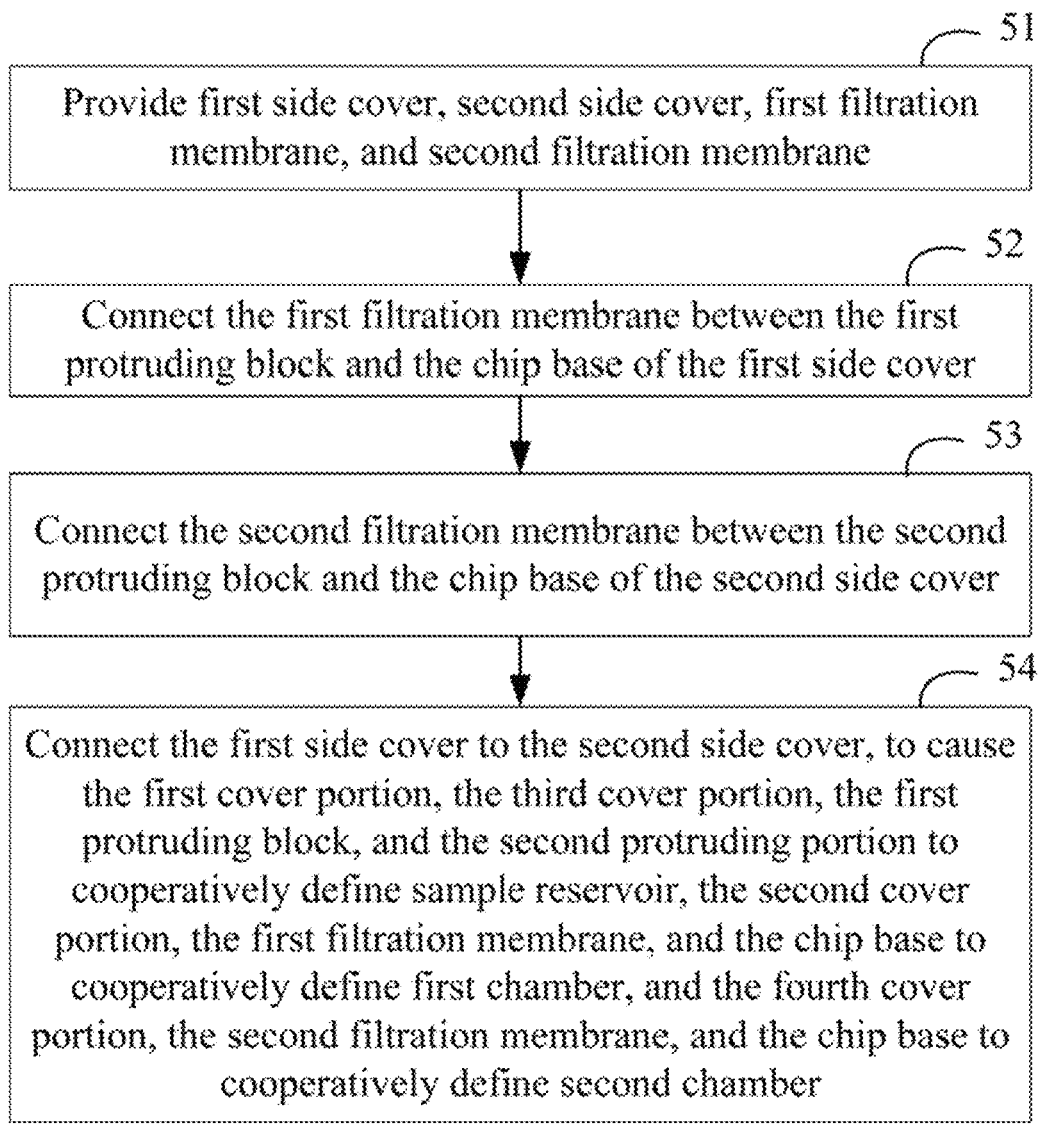
FIG. 5 is a flowchart of an embodiment of a manufacturing method of the isolation chip of FIG. 4.

FIG. 5 illustrates another embodiment of a manufacturing method of the isolation chip 10'. The method is provided by way of embodiments, as there are a variety of ways to carry out the method. The example method can begin at block 21.

At block 51, the first side cover 156, the second side cover 176, the first filtration membrane 14, and the second filtration membrane 16 are provided.

At block 52, the first filtration membrane 14 is connected between the first protruding block 154 and the chip bases 19 of the first side cover 156.

At block 53, the second filtration membrane 16 is connected between the second protruding block 174 and the chip bases 19 of the second side cover 176.

At block 54, the first side cover 156 is connected to the second side cover 176, the first protruding block 154 faces the second protruding block 174 and the two chip bases 19 face each other. Thus, the first cover portion 1561, the third cover portion 1761, the first protruding block 154, and the second protruding portion 174 cooperatively define the sample reservoir 13. The second cover portion 1562, the first filtration membrane 14, and the chip base 19 cooperatively define the first chamber 15. The fourth cover portion 1762, the second filtration membrane 16, and the chip base 19 cooperatively define the second chamber 17. Thereby, the isolation chip 10' is obtained.

Figure 6:
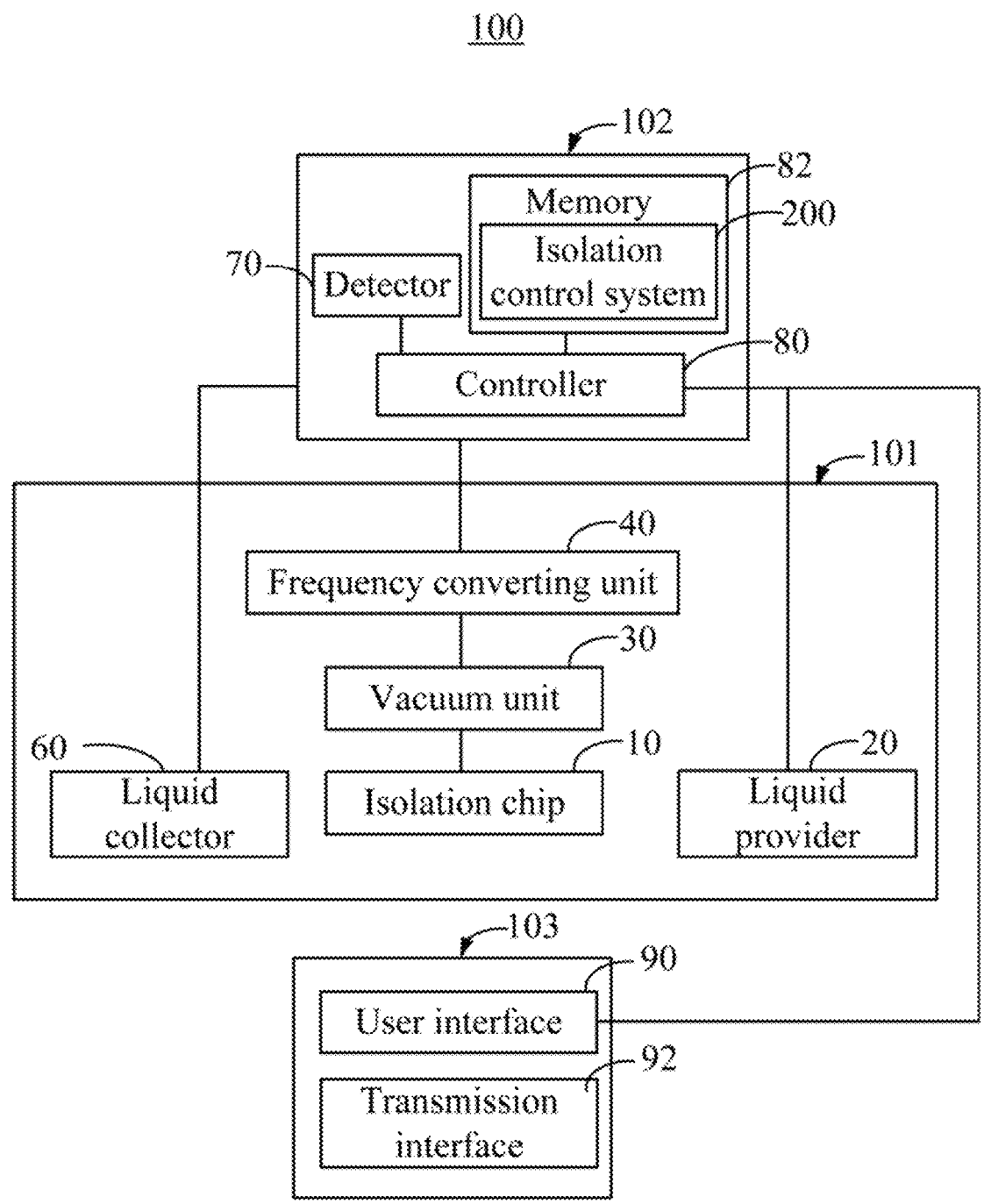
FIG. 6 is a diagrammatic view of an embodiment of an isolation device.

FIG. 6 illustrates an embodiment of an isolation device 100 including a main device portion 101, an auxiliary device portion 102, and an interaction device portion 103.

The main device portion 101 is configured to isolate and purify the target particles from the liquid sample. The main device portion 101 includes the isolation chip 10 or 10', a liquid provider 20, a vacuum unit 30, and a frequency converting unit 40.

Figure 7:
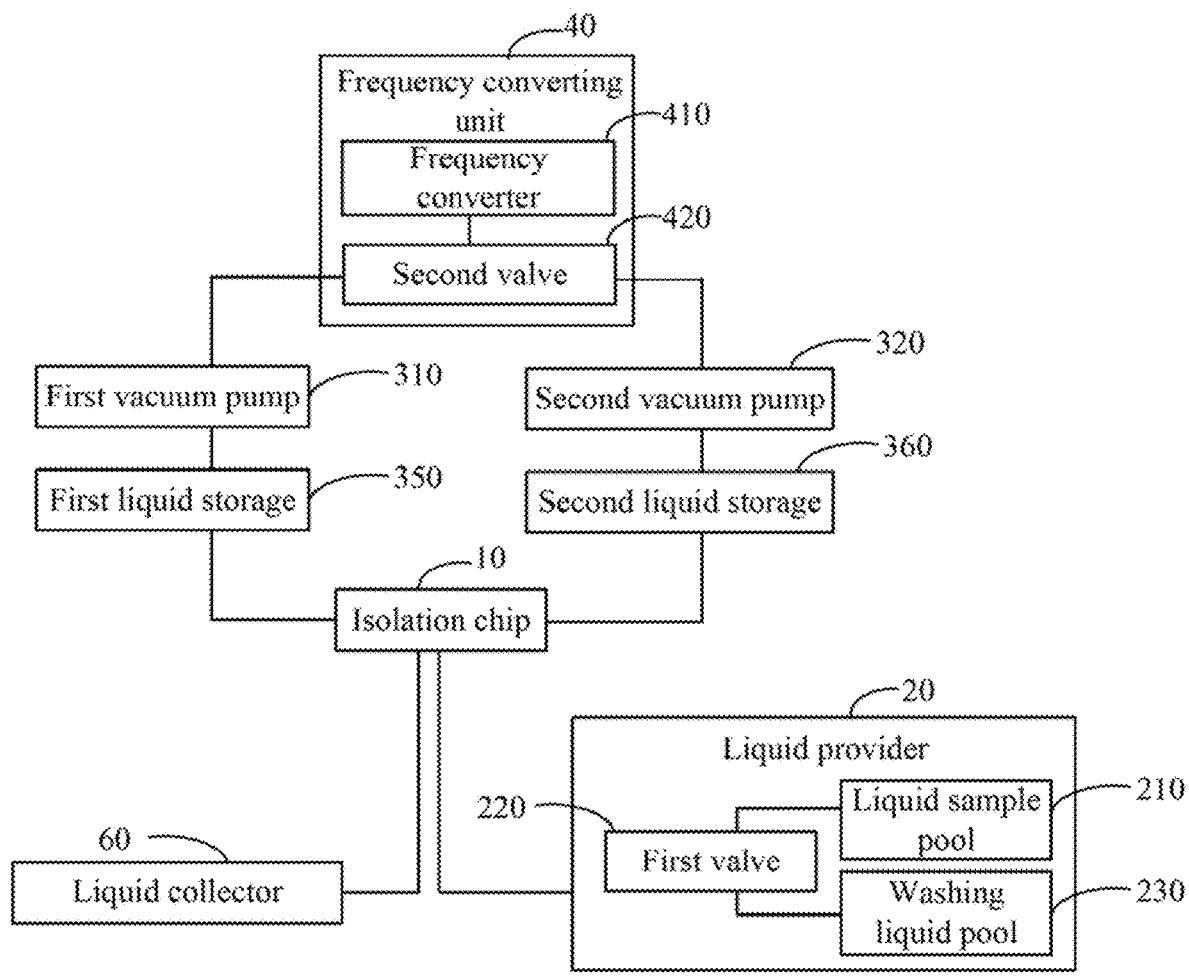
FIG. 7 is a diagrammatic view showing liquid flow paths of the isolation device of FIG. 6.

The liquid provider 20 provides the liquid sample and a washing liquid into the sample reservoir 13 of the isolation chip 10 or 10'. Referring to FIG. 7, the liquid provider 20 includes a liquid sample pool 210 for receiving the liquid sample, a washing liquid pool 230 for receiving the washing liquid, and a first valve 220. The first valve 220 is alternately switched to connect one of the liquid sample pool 210 and the washing liquid pool 230. The first valve 220 can be an electromagnetic valve or a rotary valve. When the first valve 220 connects to the liquid sample pool 210, the liquid sample in the liquid sample pool 210 can be added to the sample reservoir 13. When the first valve 220 is switched to connect to the washing liquid pool 230, the washing liquid in the washing liquid pool 230 can be added to the sample reservoir 13 to wash the isolation chip 10 or 10'. The washing liquid can include a surfactant to wash away the proteins absorbed on surfaces of the isolation chip 10 or 10'. In another embodiment, the liquid provider 20 can also be a pipette or a syringe. The liquid sample and the washing liquid can thus be manually added to the sample reservoir 13.

The vacuum unit 30 generates negative pressures in the first chamber 15 and the second chamber 17 alternately. In an embodiment, the vacuum unit 30 includes a first vacuum pump 310 and a second vacuum pump 320. The first vacuum pump 310 is connected to the first outlet 152 of the isolation chip 10 or 10'. The second vacuum pump 320 is connected to the second outlet 172 of the isolation chip 10 or 10'.

Figure 9:
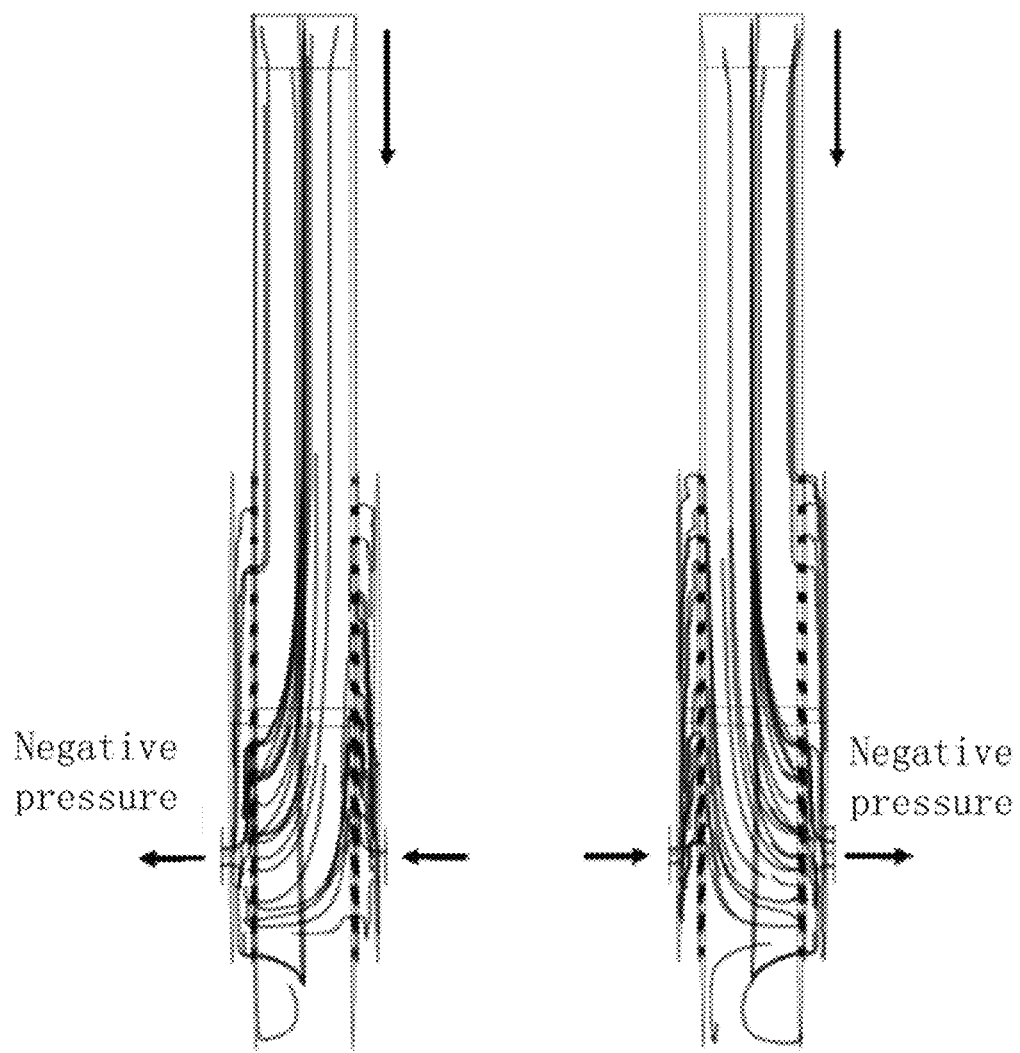
FIG. 9 is a diagrammatic view showing fluid paths in the isolation chip of FIG. 1 during sample isolation.
Figure 10A:
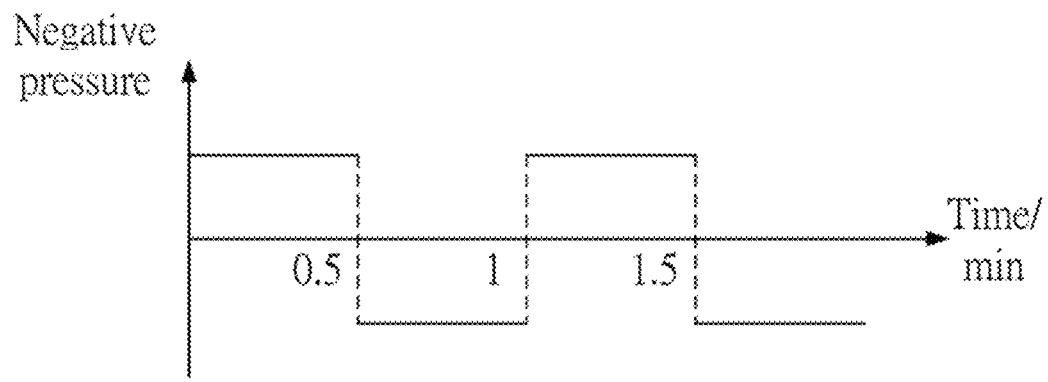
FIG. 10a is a diagram of an embodiment of negative pressure applied to the isolation chip of FIG. 1.
Figure 10B:
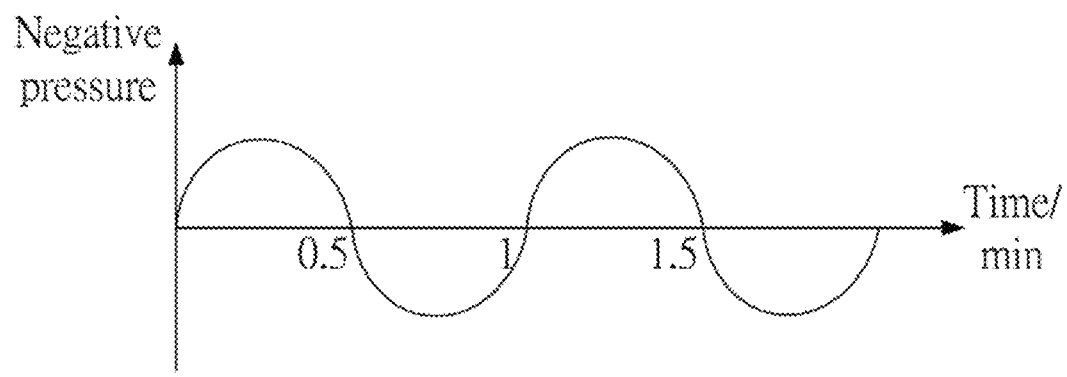
FIG. 10b is a diagram of another embodiment of negative pressure applied to the isolation chip of FIG. 1.
Figure 10C:
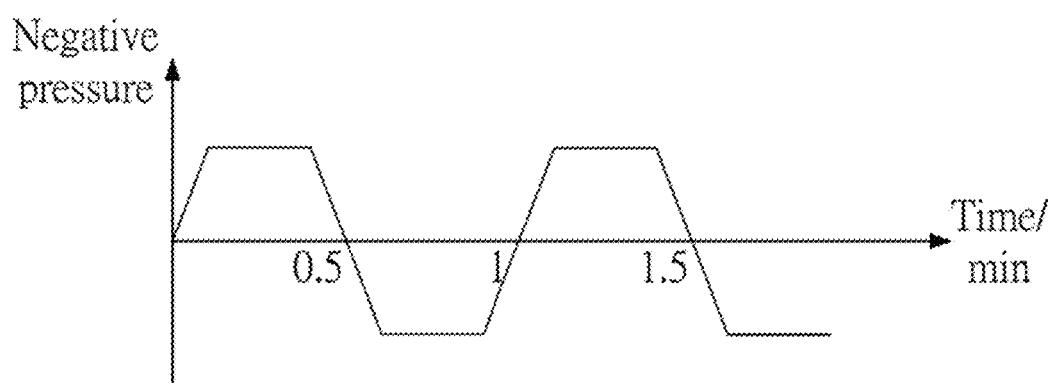
FIG. 10c is a diagram of yet another embodiment of negative pressure applied to the isolation chip of FIG. 1.

The frequency converting unit 40 is electrically connected to the vacuum unit 30, and provides electric power to the vacuum unit 30. In an embodiment, the frequency converting unit 40 includes a frequency converter 410 and a second valve 420 connected to the frequency converter 410. The second valve 420 can be an electromagnetic valve or a rotary valve. The second valve 420 is alternately switched to connect one of the first vacuum pump 310 and the second vacuum pump 320, to cause the vacuum unit 30 to alternately apply negative pressures in the first chamber 15 and the second chamber 17. That is, when the second valve 420 connects to the first vacuum pump 310, the frequency converter 410 controls the first vacuum pump 310 to generate negative pressure in the first chamber 15, corresponding to the left chamber in FIG. 9. As shown by the arrows in FIG. 9, the compositions that are smaller than the pores of the first filtration membrane 14 can pass through the first filtration membrane 14 under the negative pressure. At the same time, the back flow of the liquid sample adjacent to the second filtration membrane 16 prevents any composition from accumulating in the pores of the second filtration membrane 16. Thus, clogging of the second filtration membrane 16 can be avoided. Then, the frequency converter 410 controls the first vacuum pump 310 to stop operating, and the second valve 420 is switched to connect to the second vacuum pump 320. The frequency converter 410 controls the second vacuum pump 320 to apply negative pressures in the second chamber 17 corresponding to the right chamber in FIG. 9. As shown by the arrows in FIG. 9, the compositions that are smaller than the pores of the second filtration membrane 16 can pass through the second filtration membrane 16 under the negative pressure. At the same time, back flow of the liquid sample adjacent to the first filtration membrane 14 prevents any composition from accumulating in the pores of the first filtration membrane 14. Thus, clogging of the first filtration membrane 14 can be avoided. Then, the frequency converter 410 controls the second vacuum pump 320 to stop operating. The above procedures are repeated until complete isolation is achieved. Referring to FIG. 10a, in an embodiment, the negative pressures alternating between the first chamber 15 and the second chamber 17 are caused by rectangular wave shaped pulse signals. The rectangular wave shaped pulse signals have an amplitude of −70 kpa and a period of 1 min. Since a sudden change of direction of the rectangular wave shaped pulse signals may cause damage to the first filtration membrane 14 and the second filtration membrane 16, FIGS. 10b and 10c disclose another embodiment where shapes of the wave pulse signals can be sine wave shaped or trapezoidal wave shaped. In other embodiments, since the plasma sample may have a large amount of proteins, the vacuum unit 30 can apply a positive pressure in one of the first or the second chamber when applying a negative pressure in another one of the first or the second chamber. By applying such positive pressure, the vacuum unit 30 also improves the back flow at the first filtration membrane 14 or the second filtration membrane 16, to further avoid clogging of the first and the second filtration membranes 14 and 16. In actual use, the amplitude, the period, and the total time durations of the negative pressures can be varied according to the type of the liquid sample.

Figure 11:
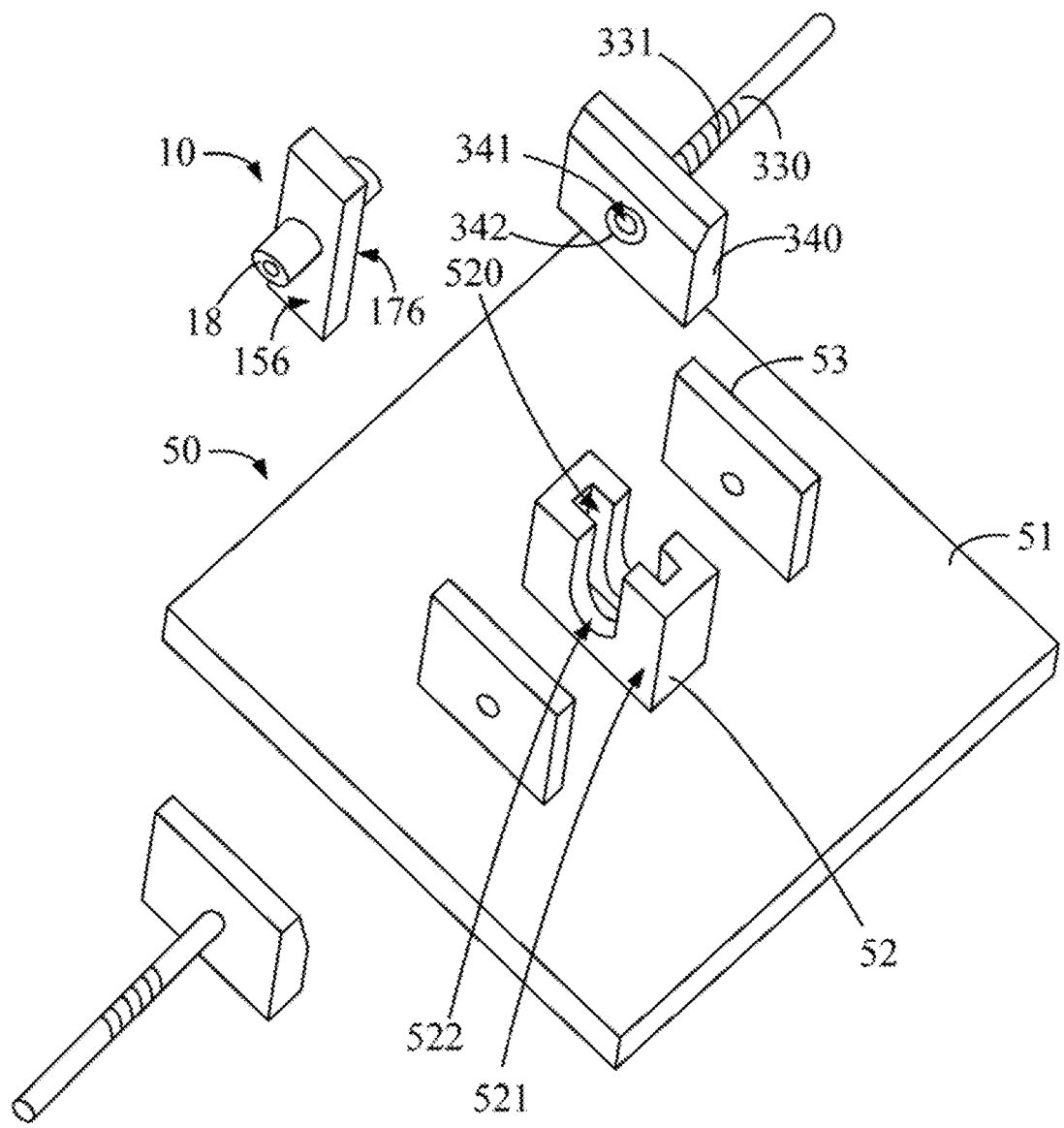
FIG. 11 is a diagrammatic view of a mounting base of the isolation device of FIG. 3.
Figure 12:
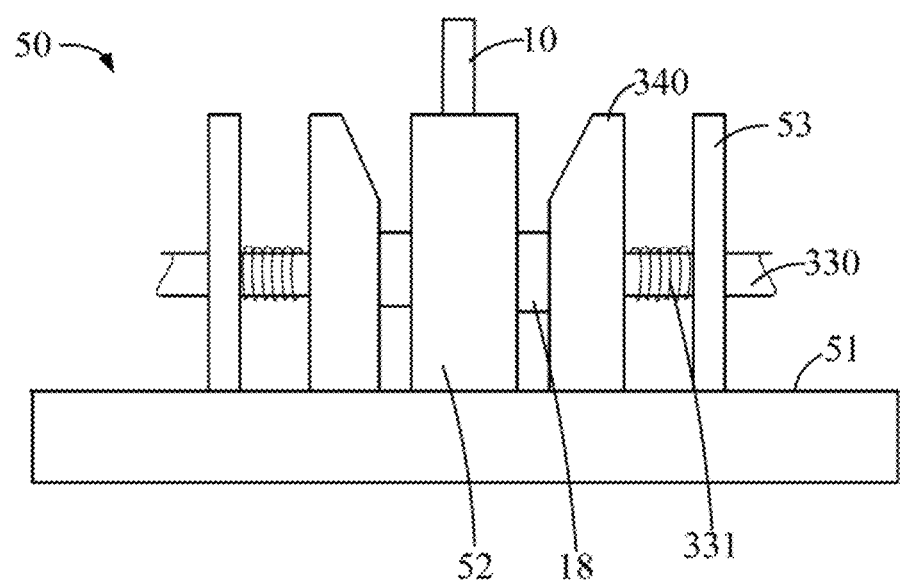
FIG. 12 is a diagrammatic view showing an isolation chip and air pipes mounted to the mounting base of FIG. 11.

Referring to FIGS. 11 and 12, in an embodiment, the main device portion 101 can further include a mounting base 50 configured for receiving the isolation chip 10 or 10'. The mounting base 50 includes a bottom plate 51, a mounting body 52, and two connecting plates 53 each mounted on the bottom plate 51. The mounting body 52 defines a receiving groove 520 for receiving the isolation chip 10 or 10'. The mounting body 52 further includes two sidewalls 521 opposite to each other. A top of each of the sidewalls 521 facing away from the bottom plate 51 defines a slot 522. When the isolation chip 10 or 10' is received in the receiving groove 520, each of the outlet connecting blocks 18 of the isolation chip 10 or 10' is received in one of the slot 522. Referring to FIG. 8b, each of the outlet connecting blocks 18 is thicker than each of the sidewalls 521, so the outlet connecting block 18 protrudes from the slot 522 when the outlet connecting block 18 is received in the slot 522.

The connecting plates 53 are positioned at opposite ends of the mounting body 52. Each of the first vacuum pump 310 and the second vacuum pump 320 includes an air pipe 330 and a pipe connecting block 340 connected to an end of the air pipe 330 facing away from the first vacuum pump 310 or the second vacuum pump 320. The pipe connecting block 340 defines a third outlet 341 that is aligned with the air pipe 330. Each air pipe 330 passes through one connecting plate 53, to position the pipe connecting block 340 between the connecting plate 53 and the mounting body 52. A spiral spring 331, positioned between the connecting plate 53 and the pipe connecting block 340, surrounds each air pipe 330. When the isolation chip 10 or 10' is received in the receiving groove 520, the first outlet 152 and the second outlet 172 are aligned with the third outlet 341. Since each outlet connecting block 18 protrudes from the slot 522, the outlet connecting block 18 can push the pipe connecting block 340 to move towards the connecting plate 53 to compress the spiral spring 331. The spiral spring 331 then rebounds to resist the isolation chip 10 or 10' against the pipe connecting block 340. Air leakage between the isolation chip 10 or 10' and the pipe connecting block 340 is thus prevented. In an embodiment, the pipe connecting block 340 includes an sealing ring 340 surrounding the third outlet 341. The sealing ring 340 can further improve airtightness between the isolation chip 10 or 10' and the pipe connecting block 340.

Referring to FIGS. 6 and 7, in an embodiment, the main device portion 101 further includes a liquid collector 60. The liquid collector 60 collects the target particles after isolation from the sample reservoir 13. The liquid collector 60 can include a sampling needle that can be inserted into the sample reservoir 13 to collect the target particles after isolation.

Furthermore, referring to FIG. 7, the main device portion 101 further includes a first liquid storage 350 and a second liquid storage 360. The first liquid storage 350 is connected between the first vacuum pipe 310 and the first outlet 152 of the isolation chip 10 or 10', and is connected to the first chamber 15 through the first outlet 152. The second liquid storage 360 is connected between the second vacuum pipe 320 and the second outlet 172 of the isolation chip 10 or 10', and is connected to the second chamber 17 through the second outlet 172. The first liquid storage 350 and the second liquid storage 360 prevent the liquid sample from flowing into the first vacuum pump 310 and the second vacuum pump 320.

The auxiliary device portion 102 is configured to ensure the isolation device 100 operates normally and efficiently. The auxiliary device portion 102 includes a detector 70 and a controller 80.

The detector 70 detects a liquid level of the liquid sample in the sample reservoir 13.

The controller 80 is electrically connected to the detector 70 and the frequency converting unit 40. The controller 80 obtains the detected liquid level, and determines whether isolation of the liquid sample is finished according to the obtained liquid level and a first preset amount of the liquid sample. The obtained liquid level corresponds to a remaining amount of the liquid sample. The first preset amount corresponds to an input amount of the liquid sample, which is usually greater than the remaining amount of the liquid sample. When isolation of the liquid sample is finished, the controller 80 controls the frequency converting unit 40 to stop generating negative pressures in the first chamber 15 and the second chamber 17. The controller 80 can be a central processing unit (CPU), a microprocessor, or other data processor chip. In an embodiment, the controller 80 controls the frequency converting unit 40 to generate negative pressures in the first chamber 15 and the second chamber 17 according to preset pressure data. The controller 80 further controls a time interval for connecting the first valve 220 and the liquid sample pool 210 according to the first preset amount of the liquid sample, thereby allowing the liquid sample with the first preset amount to be added to the sample reservoir 13. The controller 80 further controls a time interval for connecting the first valve 220 and the washing liquid pool 230 according to a second preset amount of the washing liquid, thereby allowing the washing liquid with the second preset amount to be added to the sample reservoir 13.

The interaction device portion 103 allows target particles isolation from the liquid sample to meet actual need. The interaction device portion 103 includes a user interface 90 for the user to input data related to the isolation processes through an input unit (for example, a mouse or a keyboard) of the isolation device 100. That is, the user can preset the data related to the isolation processes through the user interface 90. In an embodiment, the data related to the isolation processes includes the first preset amount of the liquid sample, the second preset amount of the washing liquid, and the preset pressure data. The preset pressure data includes the amplitude, the period, and the total time durations of the negative pressures. The controller 80 is further electrically connected to the user interface 90. Thus, the controller 80 can obtain the input data from the user interface 90, and control the frequency converting unit 40 or the liquid provider 20 to operate accordingly.

In an embodiment, the interaction device portion 103 can further include a transmission interface 92 configured to connect the isolation device 100 to a peripheral device (for example, a smart phone or a USB flash disk). The isolation device 100 can transmit data related to the isolation processes to the peripheral device through the transmission interface 92. Thus, the user can review the data related to the isolation processes after sample isolation. The transmission interface 92 can be a USB interface or a wireless interface.

Figure 8:
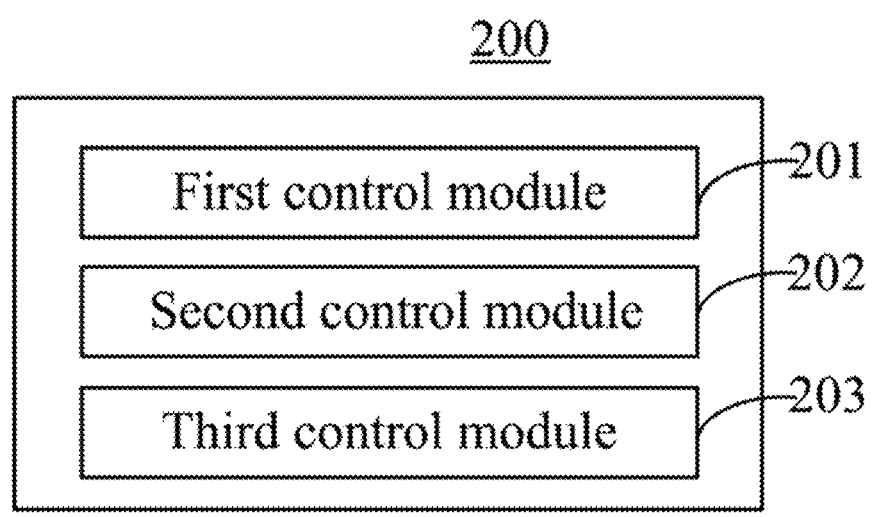
FIG. 8 is a block diagram of an isolation control system of the isolation device of FIG. 6.

The auxiliary device portion 102 further includes a memory 82. The memory 82 stores an isolation control system 200. The isolation control system 200 includes a number of modules, which are a collection of software instructions executable by the controller 80 to perform the function of the isolation control system 200. Referring to FIG. 8, the isolation control system 200 includes a second control module 202 and a third control module 203.

The second control module 202 controls the liquid provider 20 to provide the liquid sample and a washing liquid into the sample reservoir 13 of the isolation chip 10 or 10'. In an embodiment, the liquid provider 20 includes a liquid sample pool 210 for receiving the liquid sample, a washing liquid pool 230 for receiving the washing liquid, and a first valve 220. The first valve 220 is alternately switched to connect one of the liquid sample pool 210 and the washing liquid pool 230. The second control module 202 controls the first valve 220 to connect to one of one of the liquid sample pool 210 and the washing liquid pool 230, thereby allowing the liquid sample or the washing liquid to be added to the sample reservoir 13.

The third module 203 controls the vacuum unit 30 generates negative pressures in the first chamber 15 and the second chamber 17 alternately through the frequency converting unit 40. In an embodiment, the vacuum unit 30 includes a first vacuum pump 310 and a second vacuum pump 320. The first vacuum pump 310 is connected to the first outlet 152 of the isolation chip 10 or 10'. The second vacuum pump 320 is connected to the second outlet 172 of the isolation chip 10 or 10'. The frequency converting unit 40 includes a frequency converter 410 and a second valve 420 connected to the frequency converter 410. The third control module 203 controls the second valve 420 to connect one of the first vacuum pump 310 and the second vacuum pump 320, to cause the vacuum unit 30 to alternately apply negative pressures in the first chamber 15 and the second chamber 17.

In an embodiment, the isolation device 100 further includes a liquid collector 60. The second control module 202 further controls the liquid collector 60 to collect the target particles after isolation from the sample reservoir 13.

In an embodiment, the isolation device 100 further includes a detector 700. The detector 70 detects a liquid level of the liquid sample in the sample reservoir 13. The isolation control system 200 further includes a first control module 201. The first control module 201 obtains the detected liquid level from the detector 70, and determines whether isolation of the liquid sample is finished according to the obtained liquid level and a first preset amount of the liquid sample. When isolation of the liquid sample is finished, the first control module 201 sends a stop command to the third control module 203. The third control module 203 responds to the stop command, and control the frequency converting unit 40 to stop generating negative pressures in the first chamber 15 and the second chamber 17.

In an embodiment, the first control module 201 further obtains the preset pressure data, and sends a control command including the preset pressure data to the third control module 203. The third control module 203 responds to the first control command, and controls the frequency converting unit 40 to generate negative pressures in the first chamber 15 and the second chamber 17 according to preset pressure data. The first control module 201 further obtains the first preset amount of the liquid sample, and sends a second control command including the first preset amount to the second control module 202. The second control module 202 responds to the second control command, and controls a time interval for connecting the first valve 220 and the liquid sample pool 210 according to the first preset amount, thereby allowing the liquid sample with the first preset amount to be added to the sample reservoir 13. The first control module 201 further obtains the second preset amount of the washing liquid, and sends a third control command including the second preset amount to the second control module 202. The second control module 202 responds to the third control command, and controls a time interval for connecting the first valve 220 and the washing liquid pool 230 according to the second preset amount, thereby allowing the washing liquid with the second preset amount to be added to the sample reservoir 13

Figure 13:
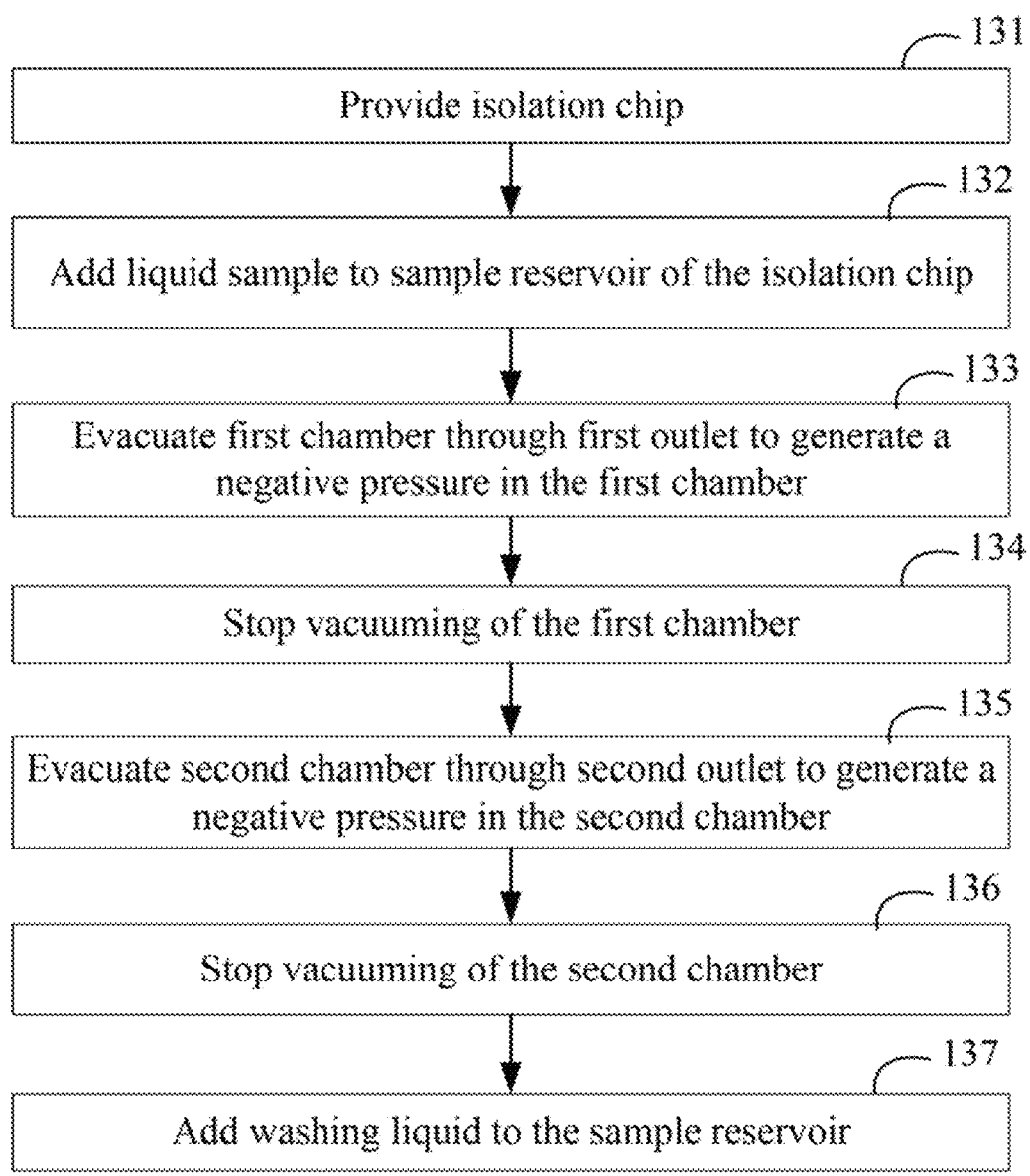
FIG. 13 is a flowchart of an isolating method of target particles from liquid sample.
Figure 14A:
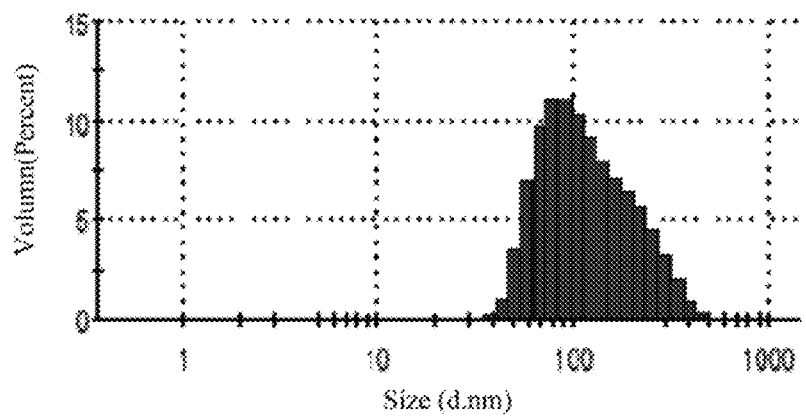
FIG. 14a is a diagram showing a particle size distribution in an original urine sample.
Figure 14B:
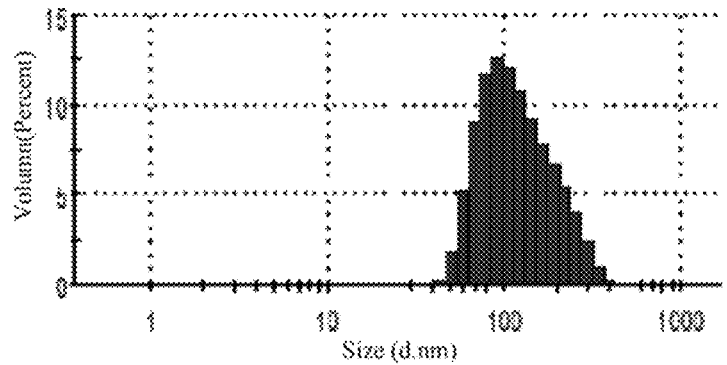
FIG. 14b is a diagram showing a particle size distribution of exosomes isolated from the urine sample by the isolation chip of FIG. 1.
Figure 14C:
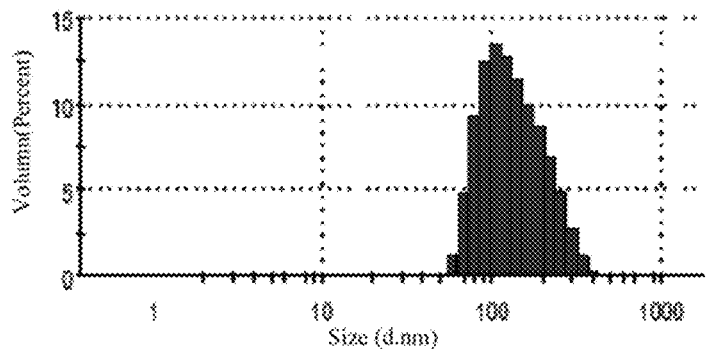
FIG. 14c is a diagram showing a particle size distribution of exosomes isolated from the urine sample by qEV™ column (iZON Science).
Figure 14D:
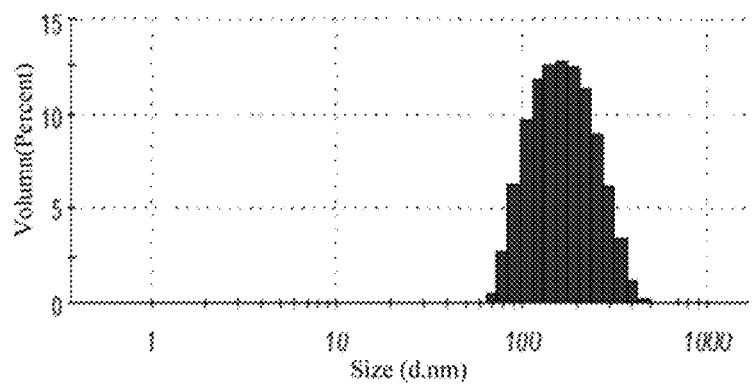
FIG. 14d is a diagram showing a particle size distribution of exosomes isolated from the urine sample by ExoQuick-TC™ exosome precipitation reagent (SBI).
Figure 14E:
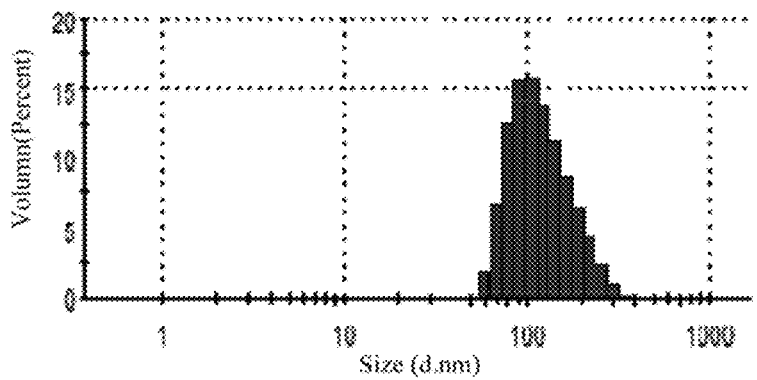
FIG. 14e is a diagram showing a particle size distribution of exosomes isolated from the urine sample by Magcapture™ exosome isolation kit (Wako).
Figure 14F:
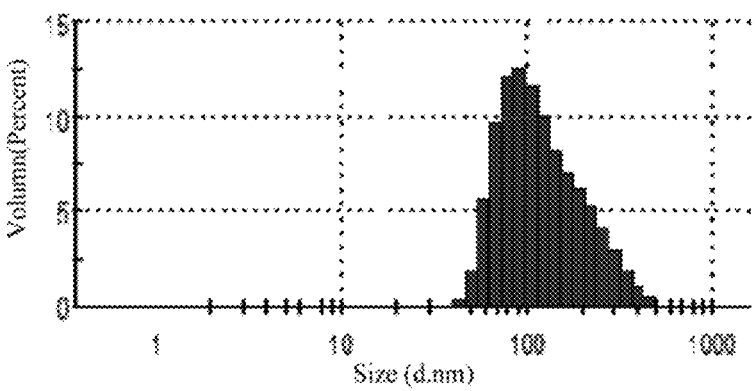
FIG. 14f is a diagram showing a particle size distribution of exosomes isolated from the urine sample by Exo-Spin™ purification kit (Cell Guidance System).

FIG. 13 illustrates an embodiment of an isolation method of target particles from liquid sample. The method is provided by way of embodiment, as there are a variety of ways to carry out the method. The method can begin at block 131.

At block 131, the isolation chip 10 or 10' is provided.

At block 132, the liquid sample is added to the sample reservoir 13 of the isolation chip 10 or 10'.

In an embodiment, the liquid sample is added to the sample reservoir 13 by the liquid provider 20. The liquid sample can be added to the sample reservoir 13 through the inlet 138. To prevent the proteins from absorbing on the pores of the first filtration membrane 14 and the second filtration membrane 16, a surfactant and a PBS buffer are further added to the sample reservoir 13. The surfactant can be Tween-20 or Pluronic F68. The surfactant can have a weight percentage of about 5%.

At block 133, the first chamber 15 is evacuated through the first outlet 152 to generate a negative pressure in the first chamber 15.

In an embodiment, before evacuating the first chamber 15, the first outlet 152 and the second outlet 172 are connected to the vacuum unit 30. Then, the vacuum unit 30 evacuates the first chamber 15 through the first chamber 15, to cause the compositions having sizes which are smaller than sizes of the pores of the first filtration membrane 14 to enter the first chamber 15 through the first filtration membrane 14. When the first chamber 15 has a small volume or when the negative pressure is switched too fast, the compositions can also enter the first liquid storage 350 through the first outlet 152.

In one embodiment, before evacuating the first chamber 15, when the liquid sample is added to the sample reservoir 13 through the inlet 138, the inlet 138 can be closed. When the inlet 138 is closed, the back flow of the liquid sample adjacent to the second filtration membrane 16 can be accelerated to avoid clogging of the second filtration membrane 16.

In other embodiments, since the plasma sample may have a large amount of proteins, a positive pressure can be generated in the second chamber 17 to further avoid clogging of the second filtration membrane 16.

At block 134, vacuuming of the first chamber 15 is stopped.

At block 135, the second chamber 17 is evacuated through the second outlet 172 to generate a negative pressure in the second chamber 17.

When the vacuum unit 30 evacuates the second chamber 17 through the second outlet 172, compositions which are absorbed on the first filtration membrane 14 may be separated from the first filtration membrane 14. Furthermore, the compositions having sizes which are smaller than the sizes of the pores of the second filtration membrane 16 can enter the second chamber 17 through the second filtration membrane 16. When the second chamber 17 has a small volume or when the negative pressure is switched to fast, the compositions can also enter the second liquid storage 360 through the second outlet 172. In other embodiments, the blocks 134 and 135 can also be performed simultaneously.

In other embodiments, since the plasma sample may have a large amount of proteins, a positive pressure can be generated in the first chamber 15 to further avoid blocking and clogging of the first filtration membrane 14.

At block 136, vacuuming of the second chamber 17 is stopped.

Then, the blocks 133 to 136 can be repeated for a number of times to further remove the compositions having sizes which are smaller than the sizes of the pores of the first filtration membrane 14 and the second filtration membrane 16, and causing the target particles to remain in the sample reservoir 13.

At block 137, the washing liquid is added to the sample reservoir 13. Then, the blocks 133 to 136 can be repeated for a number of times to wash the isolation chip 10 or 10'.

Using the above method to isolate and purify exosomes from a urine sample of 10 mL, a high yield of exosomes was obtained within 30 min. Furthermore, exosomes were also isolated and purified, respectively by qEV™, ExoQuick-TC™, MagCapture™, and Exo-Spin™, from the same urine sample. Then, the exosomes isolated by different approaches were tested by a particle size analyzer (Malvern). Referring to FIGS. 14a to 14f, the exosomes isolated by different approaches showed similar particle size distributions in the range of 30-150 nm, which matched the actual particle size distribution of the exosomes.

Figure 15A:
FIG. 15a is a scanning electron microscope (SEM) image of the exosomes isolated from the urine sample by the isolation chip of FIG. 1.
Figure 15B:
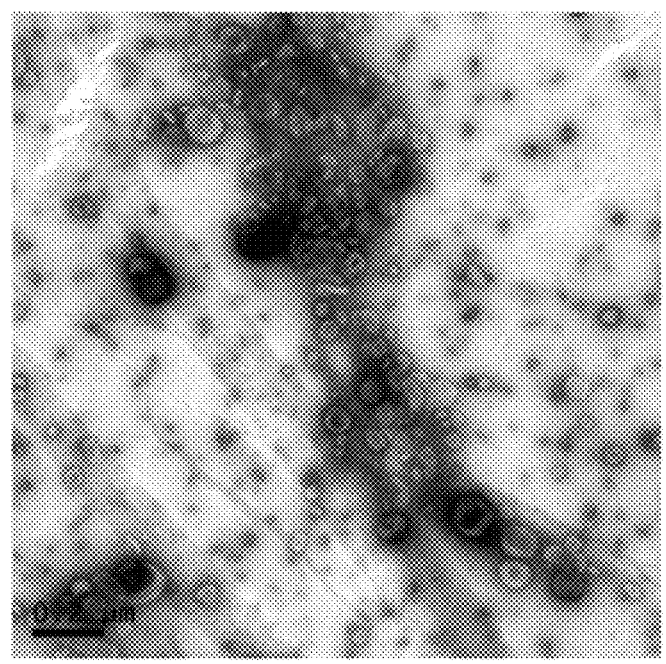
FIG. 15b is a transmission electron microscopy (TEM) image of the exosomes isolated from the urine sample by the isolation chip of FIG. 1.

The exosomes isolated by the isolation chip 10 were observed with SEM and TEM. Referring to FIGS. 15a and 15b, the exosomes after isolation had good integrity and high purity.

Figure 16:
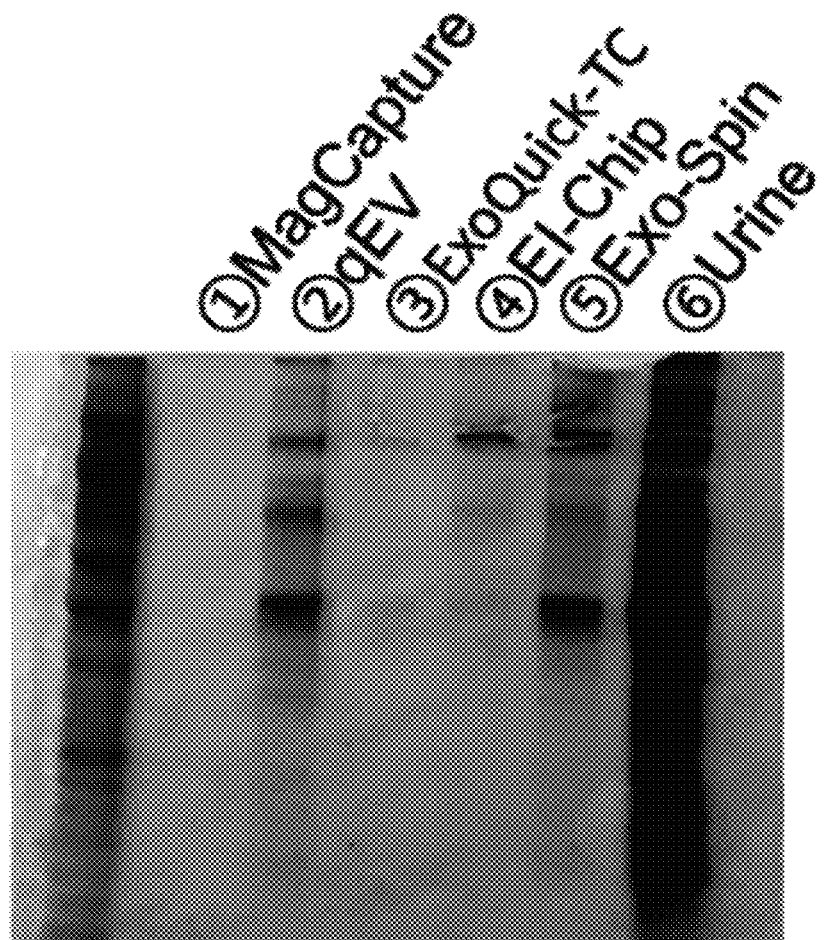
FIG. 16 is a staining image showing protein contamination in the exosomes respectively isolated by the isolation chip (labeled as EI-Chip), the qEV™, the ExoQuick-TC™, the Magcapture™, and the Exo-Spin™, after subjection to electrophoresis followed by silver staining.

Since HDLs, LDLs, IDLs, VLDL, and chylomicrons, which have similar size and density with respect to the exosomes, are difficult to be removed, to study the purity of the exosomes, the original urine sample and the exosomes obtained by different approaches were subjected to electrophoresis followed by silver staining, to identify the proteins therein. Referring to FIG. 16, the original urine sample showed strong signals, which indicated a large amount of proteins contained in the original urine sample. After isolation and purification by qEV™ and Exo-Spin™, the exosomes still showed strong signals, indicating that the exosomes still contain a large amount of proteins. After isolation and purification by MagCapture™ and ExoQuick-TC™, the majority of proteins were removed and therefore the exosomes showed much weaker signals. After isolation and purification by the isolation chip 10 (labeled as EI-Chip in the figure), the exosomes showed signals much weaker than those isolated by qEV™ and Exo-Spin™, and slightly higher than those isolated by MagCapture™ and ExoQuick-TC™. That is, the exosomes isolated by purified by the isolation chip 10 have high purity. The isolation chip 10 has competitive performance in isolating exosomes from the urine sample compared to the commercial products.

The fluid sample of a cancer patient may be different from a healthy fluid sample, and the fluid samples of different cancer patients also have different properties. To make sure that the isolation chip 10 can also be use to successfully isolate the exosomes from the fluid samples of different cancer patients, urine samples from 11 prostate cancer patients, each with 10 mL, were collected. The exosomes were respectively isolated from the urine samples by the isolation chip 10. The amount of proteins in the exosomes from different urine samples was measured with Nanodrop, and the results were shown in Table 1.

TABLE 1

| Urine samples | Amount of proteins (mg/mL) |
|---|---|
| 1 | 0.275 |
| 2 | 0.731 |
| 3 | 3.099 |
| 4 | 0.826 |
| 5 | 0.321 |
| 6 | 0.165 |
| 7 | 0.998 |
| 8 | 1.112 |
| 9 | 2.21 |
| 10 | 0.624 |
| 11 | 0.944 |

As shown in Table 1, the exosomes from 8 out of 11 urine samples have a protein concentration lower than 1 mg/mL after isolation and purification. Thus, the exosomes from most of the urine samples have a small amount of proteins, and thus have high purity.

Figure 17:
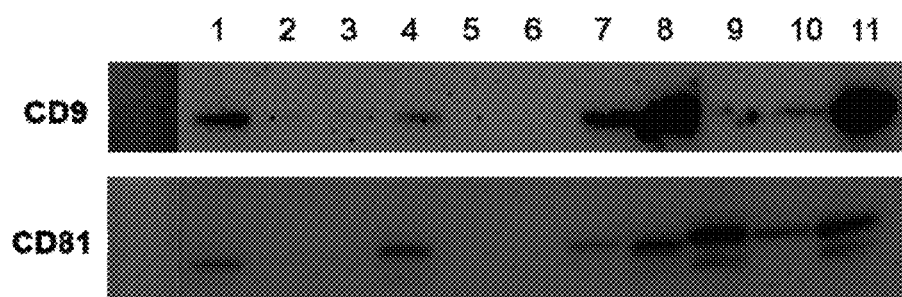
FIG. 17 is Western blot analysis of the exosomes isolated, by the isolation chip, from eleven urine samples of different cancer patients.

Furthermore, as shown in FIG. 17, Western blot analysis of the exosomes from 7 out of 11 urine samples revealed a presence of CD81 and CD9 (exosome marker), and 2 of 11 urine samples revealed a presence of one of CD81 and CD9. Thus, the isolation chip 10 can be use to successfully isolate the exosomes from the fluid samples of different cancer patients.

Moreover, to test reproducibility and robustness of the isolation chip 10, the exosomes were repeatedly isolated from the same fluid samples for 5 times by the same isolation chip 10. The amount of proteins in the exosomes from different urine samples was measured with Nanodrop. The results showed that the amount of proteins in the exosomes has a coefficient of variation smaller than 5%, compared to the data of Table 1. Thus, the isolation chip 10 has a good reproducibility for exosome isolation and purification. Furthermore, the exosomes were respectively isolated from the same fluid samples by 50 isolation chip 10, and the failure rate is smaller than 5%, which also indicates that the isolation chip 10 has a good reproducibility for exosome isolation and purification.

The embodiments shown and described above are only examples. Therefore, many commonly-known features and details are neither shown nor described. Even though numerous characteristics and advantages of the present technology have been set forth in the foregoing description, together with details of the structure and function of the present disclosure, the disclosure is illustrative only, and changes may be made in the detail, including in matters of shape, size, and arrangement of the parts within the principles of the present disclosure, up to and including the full extent established by the broad general meaning of the terms used in the claims. It will, therefore, be appreciated that the embodiments described above may be modified within the scope of the claims.

What is claimed is:

1. An isolation chip for isolation and purification of target particles from a liquid sample, comprising:
    a sample reservoir configured for receiving the liquid sample;
    a first filtration membrane comprising pores of sizes smaller than sizes of the target particles;
    a second filtration membrane comprising pores of sizes smaller than sizes of the target particles, wherein the sample reservoir is disposed between the first filtration membrane and the second filtration membrane;
    a first chamber connected to the sample reservoir through the first filtration membrane, the first chamber defining a first outlet connecting the first chamber to an ambient environment; and
    a second chamber connected to the sample reservoir through the second filtration membrane, the second chamber defining a second outlet connecting the second chamber to the ambient environment;
    wherein the sample reservoir comprises a reservoir substrate, a first inner cover, and a second inner cover, each of the first inner cover and the second inner cover is at a side of the reservoir substrate and opposite to each other, each of the first inner cover and the second inner cover define a through hole, each of the first filtration membrane and the second filtration membrane is fixedly received in each of the through holes, the first chamber comprises a first side cover facing away from the first inner cover, the first side cover and the first inner cover cooperatively define the first chamber, the first outlet is defined in the first side cover, the second chamber comprises a second side cover facing away from the second inner cover, the second side cover and the second inner cover cooperatively define the second chamber, and the second outlet is defined in the second side cover.

2. The isolation chip of claim 1, wherein each of the first side cover and the second side cover comprises an outlet connecting block, each of the outlet connecting blocks defines a channel aligned with each of the first outlet and the second outlet.

3. The isolation chip of claim 1, wherein the sample reservoir defines an inlet on top.

4. The isolation chip of claim 3, further comprising a chip base to close ends of the first chamber and the second chamber opposite to the inlet.

5. The isolation chip of claim 1, wherein the reservoir substrate, the first inner cover, the second inner cover, the first side cover, the second side cover are made of poly ethyleneimine or poly(methyl methacrylate).

6. The isolation chip of claim 1, wherein the first side cover comprises a first protruding block, the first protruding block divides the first side cover into a first cover portion and a second cover portion which are at two opposite sides of the first protruding block, the second side cover comprises a second protruding block facing the first protruding block, the second protruding block divides the second side cover into a third cover portion and a fourth cover portion which are at opposite sides of the second protruding block, the first cover portion, the third cover portion, the first protruding block, and the second protruding block cooperatively define the sample reservoir, a first chip base is connected to an end of the first side cover and faces the first protruding block, the first filtration membrane is connected between the first protruding block and the first chip base, and faces the second cover portion, the second cover portion, the first filtration membrane, and the chip base cooperatively define the first chamber, a second chip base is connected to an end of the second side cover and faces the second protruding block, the second filtration membrane is connected between the second protruding block and the second chip base and faces the fourth cover portion, the fourth cover portion, the second filtration membrane, and the second chip base cooperatively define the second chamber.

7. The isolation chip of claim 6, wherein a gap is defined between the first protruding block and the second protruding block, a flow path of the liquid sample is defined from the sample reservoir to each of the first and the second chambers through the gap.

8. The isolation chip of claim 6, wherein a surface of the first protruding block facing the first chip base defines a first mounting groove, a surface of the first chip base facing the first protruding block defines a second mounting groove, two opposite sides of the first filtration membrane are fixedly received in the first mounting groove and the second mounting groove respectively, a surface of the second protruding block facing the second chip base defines a third mounting groove, a surface of the second chip base facing the second protruding block defines a fourth mounting groove, and two opposite sides of the second filtration membrane are fixedly received in the third mounting groove and the fourth mounting groove respectively.

9. The isolation chip of claim 1, wherein each of the first filtration membrane and the second filtration membrane is made of anodic aluminum oxide.

10. A manufacturing method of an isolation chip for isolation and purification of target particles from a liquid sample, the manufacturing method comprising:
providing a reservoir substrate, a first inner cover, a second inner cover, a first side cover, a second side cover, a first filtration membrane, and a second filtration membrane, the first side cover defining a first outlet, the second side cover defining a second outlet, the first filtration membrane and the second filtration membrane comprising pores of sizes smaller than sizes of the target particles;
forming a first chamber by connecting the first side cover to a side of the first inner cover, the first outlet connecting the first chamber to an ambient environment;
connecting the first filtration membrane to the first inner cover;
forming a sample reservoir by successively connecting the reservoir substrate and the second inner cover to a side of the first inner cover facing away from the first side cover, thereby forming a flow path from the first chamber being to the sample reservoir through the first filtration membrane;
connecting the second filtration membrane to the second inner cover, wherein the sample reservoir is disposed between the first filtration membrane and the second filtration membrane; and
forming a second chamber by connecting the second side cover to a side of the second inner cover facing away from the reservoir substrate, thereby forming a flow path from the second chamber to the sample reservoir through the second filtration membrane, and the second outlet connecting the second chamber to the ambient environment.

11. The manufacturing method of claim 10, wherein the reservoir substrate, the first inner cover, the second inner cover, the first side cover, the second side cover, the first filtration membrane, and the second filtration membrane are connected to each other by adhesive.

12. The manufacturing method of claim 11, wherein the adhesive is ultraviolet-cured adhesive or silicone adhesive.

13. A manufacturing method of an isolation chip for isolation and purification of target particles from a liquid sample, the manufacturing method comprising:
providing a first side cover comprising a first protruding block and a first chip base, and a second side cover comprising a second protruding block and a second chip base, wherein the first protruding block divides the first side cover into a first cover portion and a second cover portion which are at two opposite sides of the first protruding block, the second protruding block divides the second side cover into a third cover portion and a fourth cover portion which are at opposite sides of the second protruding block, the first chip base is connected to an end of the first side cover and faces the first protruding block, the second chip base is connected to an end of the second side cover and faces the second protruding block, the first side cover defining a first outlet, the second side cover defining a second outlet;
providing a first filtration membrane and a second filtration membrane, each of the first filtration membrane and the second filtration membrane having pores of sizes smaller than sizes of the target particles;
connecting the first filtration membrane between the first protruding block and the first chip base;
connecting the second filtration membrane between the second protruding block and the second chip base;
forming a sample reservoir defined between the first cover portion, the third cover portion, the first protruding block, and the second protruding block;
forming a first chamber defined between the second cover portion, the first filtration membrane, and the first chip base; and
forming a second chamber defined between the fourth cover portion, the second filtration membrane, and the second chip base;
wherein the first chamber is connected to the sample reservoir through the first filtration membrane, and the second chamber being connected to the sample reservoir through the second filtration membrane.

* * * * *